United States Patent [19]

Soderquist et al.

[11] 4,064,187

[45] Dec. 20, 1977

[54] DEHYDROGENATION CATALYSTS

[75] Inventors: Frederick J. Soderquist, Essexville; Harold D. Boyce, Coleman; William R. Butts, Essexville, all of Mich.

[73] Assignee: The Dow Chemical Company, Midland, Mich.

[21] Appl. No.: 718,726

[22] Filed: Aug. 30, 1976

[51] Int. Cl.² .................. C07C 15/00; C07C 15/10; B01J 23/94

[52] U.S. Cl. .................. 260/669 R; 252/443; 252/468

[58] Field of Search .............. 252/470, 443, 468; 260/669 R

[56] References Cited

U.S. PATENT DOCUMENTS 3,849,339  11/1974  Turley et al. .............. 252/470
3,872,027  3/1975   Christmann et al. .......... 252/470

Primary Examiner—Winston A. Douglas
Assistant Examiner—P. E. Konopka
Attorney, Agent, or Firm—Glwynn R. Baker

[57] ABSTRACT

Self-regenerative dehydrogenation catalysts containing major proportions of $Fe_2O_3$ and ZnO and lesser amounts of alkali metal chromate and, optionally, cuprous oxide promoters together with a basic potassium-water-gas reaction promoter are improved in several respects when the basic potassium promoter is increased to 18–35 percent calculated as $K_2CO_3$ based on the active ingredients. Significantly lower ratios of steam to hydrocarbon are thereby made practical and in the dehydrogenation of meta and paraethyltoluene to vinyltoluene, less "popcorn" polymer is formed in the product stream with these high $K_2CO_3$ catalysts.

9 Claims, No Drawings

DEHYDROGENATION CATALYSTS

BACKGROUND OF THE INVENTION

This invention relates to an improved catalyst composition useful for the production of vinyl aromatic monomers by the steam dehydrogenation of their alkyl aromatic counterparts. More specifically, the invention relates to new self-regenerative catalysts and a process for using them to obtain more efficient dehydrogenation of alkylbenzenes, alkylbiphenyls, and alkylnaphthalenes.

Self-regenerative catalysts of the prior art have been based primarily on ferric oxide or copper chromite with more or less potassium added, usually in the form of potassium carbonate, to promote the water-gas reaction and thereby to prevent the catalyst from being choked with deposited carbon. Representative prior art showing such catalysts includes U.S. Pat. Nos. 2,870,228; 2,916,531; 3,179,706; and 3,703,593. Some of these patents describe broadly ferric oxide-based catalysts containing as much as 55 percent $K_2CO_3$. The well-known Shell 205 dehydrogenation catalyst, for example, contains about 35 percent $K_2CO_3$. With gross amounts of potassium promoter such as this, it is possible to use somewhat lower steam to hydrocarbon ratios in the dehydrogenation of alkyl aromatics. With Shell 105 catalyst which contains about 14 percent $K_2CO_3$ and using an externally heated reactor, the dehydrogenation of ethylbenzene to styrene can be carried out successfully with a 1:1 steam:hydrocarbon ratio. However, these catalysts based primarily on $Fe_2O_3$ have not proven entirely satisfactory for the production of substituted styrenes such as vinyltoluene.

In recent years, improved catalysts of this general type based on a mixture of ferric and zinc oxides have been described, by two of us and another in U.S. Pat. No. 3,205,179 and by one of us an two others in U.S. Pat. No. 3,907,916. In U.S. Pat. No. 3,205,179 and $Fe_2O_3$-ZnO catalyst containing 9 percent $K_2CO_3$ is specifically disclosed in connection with the process of catalyst activation by roasting or calcining under particular conditions therein claimed. The patent discloses the use of this catalyst for the steam dehydrogenation of ethylbenzene, with good results obtained at a steam:hydrocarbon feed ratio of 1.9:1. More recent commercial production of styrene with this and other available catalysts typically uses about a 1:1 ratio of steam to hydrocarbon feed. In U.S. Pat. No. 3,907,916 which claims a method for periodically reactivating such catalysts by steaming, $Fe_2O_3$-ZnO catalysts containing up to 22.5 percent $K_2CO_3$ are disclosed and one such catalyst is specifically shown to provide good results in the dehydrogenation of ethyltoluene using a steam:hydrocarbon feed ratio of 1.7:1. However, a steam ratio of about 3:1 has been the standard condition in commercial dehydrogenation of ethyltoluene to vinyltoluene.

SUMMARY OF THE INVENTION

It has now been found that unexpected improved properties are obtained in a self-regenerative catalyst composition for the steam dehydrogenation of lower alkyl aromatic hydrocarbons prepared by combining about 55-75 percent by weight of $Fe_2O_3$ and ZnO in approximately equal weight proportions, about 8-12 percent of a sodium or potassium chromate, and about 18-35 percent of a basic potassium promoter calculated as $K_2CO_3$ as the active ingredients plus any pelleting and pore control additives as may be desired. Cuprous oxide in about the same proportion as the chromate is optionally included in the catalyst composition as an aid to longer catalytic life. The $K_2CO_3$ component should remain at a proportion of 18-35 percent of the total active ingredients. The composition is formed into pellets and heated at about 110° to 650° C, preferably in the presence of steam for at least about 30 minutes. Preferably, the pellets are then calcined in the atmosphere thereby generated for about 2-24 hours at 800° to 980° C. Preferably, the $Fe_2O_3$:ZnO weight ratio is about 0.8-1.8:1 and best results are usually found at about an equal proportion of the two oxides. Iron and zinc compounds readily convertible to the oxides, for example, carbonates or oxalates, can be used in place of the oxides. Halides and silicates should be avoided in making up the catalyst composition.

DETAILED DESCRIPTION

The mechanical steps of forming, drying, and roasting the catalyst pellets described above are essentially the catalyst preparation process steps described in U.S. Pat. No. 3,205,179. The inventive feature claimed herein is a particular catalyst composition for dehydrogenating alkylaromatics and specifically the use in that composition of a defined large proportion of $K_2CO_3$ or equivalent basic potassium promoter such as $K_2O$ or KOH. The use of the catalyst for dehydrogenating alkylaromatics is another aspect of the invention.

The optimum potassium content calculated as $K_2CO_3$ is in the range of about 20-30 percent based on the total weight of active ingredients. Surprisingly, larger amounts of $K_2CO_3$ confer no added advantage and may in fact be disadvantageous. Using the defined proportion of $K_2CO_3$ or equivalent potassium compound in this catalyst composition, it has been found possible to operate commercial steam dehydrogenation units at low steam to hydrocarbon ratios heretofore thought to be impractical. Actual plant scale tests have demonstrated that this invention makes possible the dehydrogenation of ethylbenzene to styrene at a steam to hydrocarbon feed weight ratio as low as 0.5 to 1 and the corresponding dehydrogenation of ethyltoluene to vinyltoluene at a steam ratio as low as 1.5 to 1 with commercially acceptable conversion and yield and also with commercially acceptable catalyst life. Unexpectedly, although somewhat higher process temperatures may be necessary at the low steam ratios, the catalyst continues to provide satisfactory results and remains active over prolonged operating times. Under these conditions, a conventional process temperature in the range of 620° to 650° C will provide a conversion of alkyl aromatic hydrocarbon of about 40 percent with an excellent yield of vinyl aromatic product approaching 95 percent. The economic advantages and savings in energy requirements obtained by operating on a commercial scale at these steam ratios are substantial.

A further and entirely unexpected benefit found when these new catalysts are used for the dehydrogenation of methylated ethylbenzenes such as meta-and para-ethyltoluene and other such ar-methylated ethylbenzenes is the substantial reduction of the formation of undesirable lumps or granules of polymer in process lines. Such polymer, sometimes described as popcorn polymer because of its appearance, has been a major nuisance in production of these substituted styrenes using prior art catalysts becase it obstructs lines and valves and is extremely difficult to remove once formed in product recovery equipment.

While the exact mechanism of the "popcorn" polymer formation in the dehydrogenation process is not known, it is believed that a small amount of cross-linking occurs through a meta- or para-methyl group to give an insoluble polymer seed which grows by adsorption and polymerization of additional monomer. But regardless of the detailed mechanism, the discovery that formation of this "popcorn" polymer can be markedly reduced in the preparation of ar-methylstyrenes through use of these self-regenerative catalysts containing from about 18 to 35 weight percent of a basic potassium promoter calculated as $K_2CO_3$ is most advantageous. By this improved process severe and previously unavoidable process complications caused by precipitation of the "popcorn" polymer in the product recovery train can be essentially completely eliminated.

Basic potassium has been found to be specifically necessary to the success of this catalyst. When other known water-gas reaction promoters such as $Na_2CO_3$, $Li_2CO_3$, $Cs_2CO_3$ or combinations of these with $K_2CO_3$ which would be expected to be essential equivalents are substituted in the catalyst composition, the resulting catalysts are less efficient, require significantly higher process temperatures, and do not make possible the operation at lower steam ratios provided by $K_2CO_3$. These higher temperatures depress the yield of vinyl aromatic product and the advantage of the catalyst is thereby lost. These other alkali metal carbonate catalyst compositions also fail to inhibit the formation of popcorn polymer in the production of ar-methylstyrenes.

On the other hand, the chromate component can be either a sodium or potassium salt and both the chromate and the dichromate can be used. Thus, $Na_2CrO_4$, $K_2CrO_4$, $Na_2Cr_2O_7$, and $K_2Cr_2O_7$ are all equally effective and give essentially the same results when used in equivalent quantities. The optimum proportions of chromate and the optional cuprous oxide are at about 15 percent of the $Fe_2O_3$-ZnO content.

In addition to the above-described active ingredients of the catalyst composition, small quantities of conventional inert pelleting aids such as lubricants, cements, and extrusion aids are normally employed to make firm, long-lasting, and suitably porous catalyst pellets. Carbonaceous lubricants and extrusion aids such as graphite and methyl cellulose ethers are preferred. These substances burn out of the catalyst pellets during the activation procedure, thereby leaving a desirably porous catalyst pellet or granule. In order to provide added pellet strength and resistance to abrasion, a refractory cement such as an alumina cement is desirable. These pelleting aids are generally employed in amounts of 1-5 percent each, based on the total weight of composition. Suitable aids of this kind are described in the examples and are also defined in U.S. Pat. No. 3,205,179.

Catalyst compositions of the invention can be formed into pellets or granules for activation and use by any conventional means, e.g., by compression pelleting of the dry composition or by extruding a paste made with water or other such volatile liquid.

The catalysts of this invention have been found to retain their effectiveness and efficiency over long periods of operation. Production plant scale tests running to many months have shown the catalyst life to be more than sufficiently long for practical commercial use. When the catalyst activation and regeneration procedures disclosed in U.S. Pat. Nos. 3,205,179 and 3,907,916 are applied, these new catalysts can have effective catalyst lives measured in years.

CATALYST PREPARATION

Active ingredients of a $ZnO$-$Fe_2O_3$ based self-regenerative dehydrogenation catalyst using various proportions of $K_2CO_3$ were combined dry with 15 percent of their total weight of pelleting additives and water was added to make a thick paste. The parts by weight of the individual ingredients calculated on the basis of an overall total of 100 were as follows:

TABLE I

| Ingredient | Catalyst No. | | | | |
|---|---|---|---|---|---|
| | 1 | 2 | 3 | 4 | 5 |
| $Fe_2O_3$ | 30.0 | 28.25 | 26.54 | 23.08 | 19.62 |
| ZnO | 30.0 | 28.25 | 26.54 | 23.08 | 19.62 |
| $Cu_2O$ | 9.0 | 8.5 | 7.96 | 6.92 | 5.88 |
| $Na_2Cr_2O_7$ | 9.0 | 8.5 | 7.96 | 6.92 | 5.88 |
| $K_2CO_3$ | 9.0 | 13.5 | 18.0 | 27.0 | 36.0 |
| Cement (1) | 3.9 | 3.9 | 3.9 | 3.9 | 3.9 |
| Graphite | 5.1 | 5.1 | 5.1 | 5.1 | 5.1 |
| Methocel (2) | 4.0 | 4.0 | 4.0 | 4.0 | 4.0 |

(1) Lumnite cement, and alumina-based cement from Atlas Mineral Products Co.
(2) Methylcellulose with 2 percent aqueous solution viscosity = 2,000–4,000 cps at 20° C.

The paste was extruded and cut into segments which were dried at 110° C to make approximately 3/16-inch pellets. These pellets were heated to 300° C in about 4 hours, steamed while heating from 300° to 600° C in about 4 hours, then the steam was shut off and the catalyst pellets were heated to 850° C (900° C for Catalyst #1) and heating at that temperature was continued for about 12 hours. The latter calcining at 600° to 850° C was done in an atmosphere of the gas generated by the catalyst during that time, essentially a mixture of carbon oxides with a small amount of hydrogen.

EXAMPLE 1

These and other catalyst compositions described hereinafter were evaluated by putting a 70 ml sample in a vertical, electrically heated reactor tube with means for feeding a vaporized mixture of steam and hydrocarbon into the top of the reactor tube and recovering the products from the bottom. The hydrocarbon feed was a 2:1 mixture of meta- and para-ethyltoluene used at a feed rate of about 31 g/hour. The catalyst temperature was adjusted as necessary with different catalysts and different ratios of steam to hydrocarbon in order to obtain a conversion of ethyltoluene of about 40 percent as determined by standard chromatographic techniques for estimating vinyltoluene.

After adjusting reactor conditions to reach an equilibrium at the desired level of conversion, a continuous run of several hundred hours was made with each catalyst and analyses were run at widely separated intervals to check performance. The data listed represent averages of two to three typical analyses.

TABLE II

| Catalyst No. | % $K_2CO_3$ (on active ingred.) | Temp. ° C | Wt. Ratio Steam/HC | % Yield |
|---|---|---|---|---|
| 1 | 10.3 | 685 | 1.5 | 86.5 |
| 2 | 15.5 | 662 | 1.5 | 83.4 |
| 3 | 20.7 | 667 | 1.42 | 89.0 |
| 4 | 31.0 | 648 | 1.49 | 92.2 |
| 5 | 41.3 | 687 | 1.44 | 87.7 |
| 1 | 10.3 | 650 | 2.0 | 93.0 |
| 2 | 15.5 | 624 | 1.94 | 92.9 |
| 3 | 20.7 | 618 | 1.93 | 93.3 |
| 4 | 31.0 | 626 | 1.93 | 93.8 |
| 5 | 41.3 | 665 | 1.91 | 91.2 |
| 1 | 10.3 | 635 | 3.0 | 94.0 |

TABLE II-continued

| Catalyst No. | % $K_2CO_3$ (on active ingred.) | Temp. ° C | Wt. Ratio Steam/HC | % Yield |
|---|---|---|---|---|
| 2 | 15.5 | 620 | 2.87 | 93.3 |
| 3 | 20.7 | 622 | 2.89 | 93.9 |
| 4 | 31.0 | 625 | 2.9 | 94.5 |
| 5 | 41.3 | 661 | 2.9 | 92.6 |

At the low steam ratio runs where these catalyst compositions show the most advantage, the optimum yield and temperature levels were found at about 30 percent $K_2CO_3$ based on the active ingredients.

EXAMPLE 2

The hydrogenation of ethylbenzene to styrene requires less steam than the corresponding dehydrogenation of ethyltoluene using a self-regenerating catalyst of the type disclosed herein. To illustrate this, a sample of the catalyst composition containing 18 percent $K_2CO_3$ (20.7 percent on an active ingredient basis) shown above was tested with ethylbenzene feed according to the same procedure described in Example 1 using progressively less steam. The data are averages of typical values determined over operating periods of 127–291 hours' duration at each steam ratio. Ethylbenzene conversion was held at or close to 40 percent as before.

TABLE III

| Wt. Ratio Steam/HC | Temp. ° C | % Yield |
|---|---|---|
| 1.02 | 619 | 94.9 |
| 0.93 | 622 | 95.0 |
| 0.81 | 623 | 94.7 |
| 0.72 | 628 | 94.2 |
| 0.62 | 642 | 92.8 |
| 0.52 | 650 | 92.5 |
| 0.45 | 700 | 80.0 |

Steam reactivation of the catalyst at about 700° C for 20 hours after the last operating period restored temperature-yield levels at 0.45 steam ratio to 625° C and 94.6 percent over about 200 hours' operating time under these conditions. However, the efficiency declined gradually after that time so that after about 500 hours' operation following the steam reactivation, the benefit of the reactivation had been lost.

EXAMPLE 3

To show the effect of $K_2CO_3$ content on popcorn polymer formation, a series of non-calcined catalysts was prepared having a similar initial composition except for the $K_2CO_3$ content by dry mixing the components in the proportions given in Table IV. Then water was added to form a paste suitable for extrusion with a conventional pellet mill using a 3/16 inch rotary die. After initial drying at room temperature the catalyst pellets were heated for at least 12 hours at 100° to 150° C.

TABLE IV

| Component | Self-Regenerative Catalysts Initial Composition, Wt. % | | | |
|---|---|---|---|---|
| | A | B | C | D |
| $Fe_2O_3$ | 32.0 | 30.0 | 24.7 | 16.5 |
| ZnO | 32.0 | 30.0 | 24.7 | 16.5 |
| $Cu_2O$ | 10.0 | 9.0 | 7.4 | 4.9 |
| $Na_2Cr_2O_7$ | 10.0 | 9.0 | 7.4 | 4.9 |
| Refractory cement[a] | 3.9 | 3.9 | 3.3 | 2.2 |
| Graphite | 5.1 | 5.1 | 4.2 | 2.8 |
| Methyl cellulose[b] | 4.0 | 4.0 | 3.3 | 2.2 |
| $K_2CO_3$ | 3.0 | 9.0 | 25.0 | 50.0 |
| | 100.0 | 100.0 | 100.0 | 100.0 |

[a]Lumnite cement from Atlas Mineral Products Co.
[b]Two percent aqueous viscosity of 2,000–4,000 cps at 20° C.

These catalysts were evaluated for the dehydrogenation of a 2:1 m:p-ethyltoluene feed using the apparatus and procedure described in Example 1.

After adjusting the reactor conditions to an ethyltoluene conversion of 40 percent, a continuous run of from about 350–450 hours was made with each test catalyst. With unused catalysts an induction period of from 10–30 hours was often observed prior to appreciable formation of "popcorn" polymer. At the end of each run the "popcorn" polymer was carefully removed from the product recovery train, collected on a suction funnel, and dried in an air stream for several hours at room temperature. Finally the polymer was held in a vacuum oven at about 25° C and at 120–140 mm for 12–16 hours and then weighed. The amount of "popcorn" polymer was calculated based on both the amount of m/p-ethyltoluene fed to the reactor and the recovered m/p-vinyltoluene.

Typical results from the catalysts described in Example 3 are given in Table V. Also included are data from two commercial catalysts, E and F, which consisted essentially of $Fe_2O_3$ and $Cr_2O_3$ with $K_2CO_3$ as promoter.

TABLE V

| | Dehydrogenation of m/p-Ethyltoluene | | |
|---|---|---|---|
| Catalyst | Wt. % $K_2CO_3$ | Wt. % "Popcorn" Polymer Based On | |
| | | m/p-Ethyltoluene | m/p-Vinyltoluene |
| A | 3.0 | 0.30 | 0.75 |
| B | 9.0 | 0.08 | 0.20 |
| C | 25.0 | 0.05; 0.17* | 0.12; 0.42* |
| D | 50.0 | 0.68 | 1.70 |
| E | 7.0 | 0.23 | 0.56 |
| F | 26.0 | 0.08 | 0.20 |

*Two determinations

Under similar conditions using o-ethyltoluene and Catalyst A, no detectable amount of "popcorn" polymer was formed. Yet with 4-ethyl-o-xylene, 5-ethyl-m-xylene and similar polymethylethylbenzenes wherein each methyl group is meta or para to the ethyl group, precipitation of the "popcorn" polymer occurs and is reduced by using a self-regenerative catalyst of the invention containing a higher $K_2CO_3$ content in the range from about 18–35 weight percent.

EXAMPLE 4

By substituting other alkali and alkaline earth metal salts for the $K_2CO_3$ in the general catalyst formulation given in Example 3, further self-regenerative catalysts were prepared to test the effectiveness of various promoters in inhibiting formation of "popcorn" polymer. Typical results for several catalysts tested as described in Example 4 are given in Table VI.

TABLE VI

| | Alkali and Alkaline Earth Promoters | |
|---|---|---|
| Promoter[a] | Wt. % "Popcorn" Polymer Based On | |
| | m/p-Ethyltoluene | m/p-Vinyltoluene |
| $K_2CO_3$ | 0.17 | 0.42 |
| $KNO_3$ | 0.40 | 1.00 |
| $Na_2CO_3$ | 1.87 | 4.73 |

TABLE VI-continued

| | Alkali and Alkaline Earth Promoters | |
|---|---|---|
| | Wt. % "Popcorn" Polymer Based On | |
| Promoter[a] | m/p-Ethyltoluene | m/p-Vinyltoluene |
| CaCO$_3$ | 1.03; 2.19 | 2.78; 5.53 |

[a] 17.0 wt. % as the respective oxide

In a similar manner it is found that potassium carbonate, potassium hydroxide, and potassium oxide are essentially equivalent in promoting both the normal self-regeneration of the catalyst and a decrease in formation of "popcorn" polymer in the dehydrogenation of m/p-ethyltoluene and other similar polyalkylbenzenes.

The self-regenerative catalysts described herein are effective generally for the steam dehydrogenation of alkylated aromatic hydrocarbons having from 1 to 2 six-membered aromatic rings, zero to 3 methyl groups, and 1 to 2 alkyl groups of 2-3 carbon atoms with a total of 8-18 carbon atoms in the hydrocarbon at a temperature of 600°-700° C. Thus, hydrocarbons such as ethylbiphenyl, ethylnaphthalene, ethyldimethylbiphenyl, isopropylbenzene, ethylxylene, diethylbenzene, and ethyltrimethylbenzene can all be dehydrogenated over this catalyst to corresponding vinylaromatic products. The catalyst is particularly useful for dehydrogenating alkyl benzenes and is most advantageous for efficiently dehydrogenating meta- and para-ethyltoluene as demonstrated herein.

We claim:

1. A self-regenerative catalyst composition for the steam dehydrogenation of lower alkyl aromatic hydrocarbons to the corresponding vinyl aromatic compounds consisting essentially of about 55-75 percent by weight of Fe$_2$O$_3$ and ZnO in a weight ratio of from about 0.8 to about 1.8 Fe$_2$O$_3$ to one of ZnO, about 8-12 percent of a sodium or potassium chromate, and a basic potassium promoter of the water gas reaction from the group consisting of K$_2$CO$_3$, K$_2$O and KOH, the improvement wherein said promoter constitutes about 18-35 percent of the total calculated as K$_2$CO$_3$.

2. The composition of claim 1 wherein the Fe$_2$O$_3$ and ZnO are present in about equal weights.

3. The composition of claim 1 which additionally includes Cu$_2$O in about the same proportion as the chromate and wherein said promoter calculated as K$_2$CO$_3$ content remains at 18-35 percent of the total listed components.

4. The composition of claim 3 wherein the said calculated K$_2$CO$_3$ content is about 20-30 percent.

5. The composition produced by heating the composition of claim 1 in the presence of steam at about 110° to 650° C for at least about 30 minutes and thereafter calcining at about 800°-980° C for about 2-24 hours in the autogenous atmosphere thereby generated.

6. In a method for dehydrogenating an alkylated aromatic hydrocarbon having from 1 to 2 six-membered rings, zero to 3 methyl groups and 1 to 2 alkyl groups of 2 to 3 carbon atoms each and a total of 8-18 carbon atoms in said hydrocarbon in the presnce of steam at 600°-700° C by passing a mixture of steam and the vaporized hydrocarbon over a self-regenerative catalyst, the improvement wherein the catalyst is that defined in claim 1.

7. The method of claim 6 wherein the aromatic hydrocarbon is an alkylated benzene.

8. The method of claim 7 wherein the aromatic hydrocarbon is ethyltoluene.

9. The method of claim 7 wherein the aromatic hydrocarbon is ethylbenzene.

* * * * *

UNITED STATES PATENT OFFICE
CERTIFICATE OF CORRECTION

Patent No. 4,064,187  Dated December 20, 1977

Inventor(s) Frederick J. Soderquist, Harold D. Boyce, and William R. Butts

It is certified that error appears in the above-identified patent and that said Letters Patent are hereby corrected as shown below:

Column 1, line 38, delete "an" before the word "two" and insert --and--.

Column 1, line 39, delete "and" and insert --an--.

Column 2, line 4, delete "catalytic" and insert --catalyst--.

Column 2, line 15, delete "oxolates" and insert --oxalates--.

Column 2, line 68, delete "becase" and insert --because--.

Column 4, line 22 under Table I, delete "and" and insert --an--.

Column 7, line 30 in Claim 1, after the number "1." delete "A" and insert --In a--.

Column 8, line 24, delete "presnce" and insert --presence--.

Signed and Sealed this

Thirtieth Day of May 1978

[SEAL]

Attest:

RUTH C. MASON  
Attesting Officer

LUTRELLE F. PARKER  
Acting Commissioner of Patents and Trademarks